United States Patent
Krimsky

(10) Patent No.: US 10,881,466 B2
(45) Date of Patent: Jan. 5, 2021

(54) SYSTEMS, METHODS, AND COMPUTER-READABLE MEDIA OF PROVIDING DISTANCE, ORIENTATION FEEDBACK AND MOTION COMPENSATION WHILE NAVIGATING IN 3D

(71) Applicant: COVIDIEN LP, Mansfield, MA (US)

(72) Inventor: William S. Krimsky, Bel Air, MD (US)

(73) Assignee: COVIDIEN LP, Mansfield, MA (US)

( * ) Notice: Subject to any disclaimer, the term of this patent is extended or adjusted under 35 U.S.C. 154(b) by 630 days.

(21) Appl. No.: 15/250,266

(22) Filed: Aug. 29, 2016

(65) Prior Publication Data

US 2018/0055574 A1    Mar. 1, 2018

(51) Int. Cl.

| | | |
|---|---|---|
| A61B 34/20 | (2016.01) | |
| A61B 34/10 | (2016.01) | |
| A61B 34/00 | (2016.01) | |
| A61B 90/00 | (2016.01) | |
| A61B 5/113 | (2006.01) | |
| A61B 10/00 | (2006.01) | |
| A61B 17/00 | (2006.01) | |

(52) U.S. Cl.
CPC .............. *A61B 34/20* (2016.02); *A61B 5/113* (2013.01); *A61B 10/00* (2013.01); *A61B 34/10* (2016.02); *A61B 34/25* (2016.02); *A61B 90/37* (2016.02); *A61B 2017/00699* (2013.01); *A61B 2017/00809* (2013.01); *A61B 2034/107* (2016.02); *A61B 2034/2051* (2016.02); *A61B 2034/254* (2016.02); *A61B 2034/256* (2016.02)

(58) Field of Classification Search
None
See application file for complete search history.

(56) References Cited

U.S. PATENT DOCUMENTS

| | | |
|---|---|---|
| 4,043,324 A | 8/1977 | Shaw, IV |
| 4,150,292 A | 4/1979 | Ter-Pogossian |
| 4,629,989 A | 12/1986 | Riehl et al. |

(Continued)

FOREIGN PATENT DOCUMENTS

| | | |
|---|---|---|
| WO | 2015164587 A2 | 10/2015 |
| WO | 2016/004177 A1 | 1/2016 |

OTHER PUBLICATIONS

ISR for PCT/US06/13813, Oct. 2, 2006, D'Souza.

(Continued)

*Primary Examiner* — Kaylee R Wilson
*Assistant Examiner* — Jay B Shah

(57) ABSTRACT

A system for navigating to and interacting with a region of interest during a respiratory cycle is provided. The system includes an extended working channel, a computing device including a memory and at least one processor, a plurality of images stored in the memory, a display device that displays a user interface. The user interface includes at least one image of the plurality of images depicting the region of interest and a progression of the extended working channel through the airway, and a probability diagnostic and/or treatment zone defining a probable distribution of a trajectory of the tool once deployed beyond an opening of the extended working channel displayed in the at least one image. The respiratory cycle is divided into inhalation and exhalation. The user interface is configured to depict movement of the region of interest and the airways during the respiratory cycle.

19 Claims, 7 Drawing Sheets

(56) References Cited

U.S. PATENT DOCUMENTS

| | | |
|---|---|---|
| 5,090,401 A | 2/1992 | Schwieker |
| 5,099,855 A | 3/1992 | Yount |
| 5,784,431 A | 7/1998 | Kalend et al. |
| 6,279,579 B1 | 8/2001 | Riaziat et al. |
| 6,292,682 B1 | 9/2001 | Kruger |
| 6,374,667 B1 | 4/2002 | Eriksen et al. |
| 6,731,970 B2 | 5/2004 | Schlossbauer et al. |
| 7,154,991 B2 | 12/2006 | Earnst et al. |
| 7,221,733 B1 | 5/2007 | Takai et al. |
| 8,042,209 B2 | 10/2011 | D'Souza et al. |
| 2005/0182295 A1 | 8/2005 | Soper et al. |
| 2011/0160569 A1 | 6/2011 | Cohen et al. |
| 2015/0305650 A1* | 10/2015 | Hunter ............... A61B 1/0005 600/424 |
| 2016/0000520 A1* | 1/2016 | Lachmanovich ...... A61B 34/20 600/424 |

OTHER PUBLICATIONS

D'Souza et al., "Real-time intra-fraction-motion tracking using the treatment couch: a feasibility study," Abstract, Physics Med. Biol. 50: 1-13 (2005).

D'Souza et al., "An analysis of the treatment couch and control system dynamics for respiration-induced motion compensation," Abstract, Am. Assoc. Phys. Med. 33(12): 4701-4709 (2006).

European Search Report dated Jan. 19, 2018 issued in European Patent Application No. 17187480.3.

Examination Report for Application No. 17 187 480.3 dated Feb. 20, 2020.

\* cited by examiner

SYSTEMS, METHODS, AND COMPUTER-READABLE MEDIA OF PROVIDING DISTANCE, ORIENTATION FEEDBACK AND MOTION COMPENSATION WHILE NAVIGATING IN 3D

BACKGROUND

Technical Field

The present disclosure relates to a devices, systems, methods, and computer-readable media for enabling navigation to a region of interest within or outside of an airway (or to which access is otherwise limited) during the respiratory cycle. During the respiratory cycle, respiratory motion via inhalation and exhalation, coughing, vascular or cardiac pulsations, cause movement of regions of interests within and outside of the airways and the airways. The present disclosure further includes devices, systems, methods, and computer-readable media for assessing the ability of tools to better reach and interact with a region of interest as the region of interest and tools move during the respiratory cycle.

Description of Related Art

A common device for inspecting and navigating the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

In navigating to a region of interest, bronchoscopes, however, are limited in how far they may be advanced through the airways due to their size. Where the bronchoscope is too large to reach a region of interest location deep in the lungs, a clinician may utilize certain real-time imaging modalities such as fluoroscopy. Fluoroscopic images, while useful, present certain drawbacks for navigation, as it is often difficult to distinguish luminal passageways from solid tissue. Moreover, the images generated by the fluoroscope are two-dimensional whereas navigating the airways of a patient requires the ability to maneuver in three dimensions.

To address these aforementioned issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Covidien LP. The details of such a system are described in the commonly assigned U.S. Pat. No. 7,233,820 filed on Mar. 29, 2004 to Gilboa and entitled ENDOSCOPE STRUCTURES AND TECHNIQUES FOR NAVIGATING TO A TARGET IN BRANCHED STRUCTURE, the contents of which are incorporated herein by reference. While the system as described in U.S. Pat. No. 7,233,820 is quite capable, there is always a need for development of improvements and additions to such systems.

In addition, during the performance of an ENB™ procedure using an electromagnetic navigation ("EMN") system, a clinician may be required to navigate to a region of interest within or outside of an airway (or to a region of interest which access is otherwise limited). During the navigation, the catheter may have to be parked short of or transiently within the region of interest. This is done in preparation for insertion of an access tool or needle, which may have to penetrate the airway wall in order to reach the region of interest. It is very common for a clinician to prefer moving as close as possible to the region of interest. However, this sometimes overlooks the factor of catheter orientation and distance in relation to the region of interest during the respiratory cycle.

During navigation to a region of interest, a patient continues their respiratory cycle causing airway passages and regions of interest within and outside of airways to move and potentially change shape. An assessment of bronchoscope, biopsy tool, therapeutic instruments and other diagnostic instrument locations with respect to these areas during respiration is therefore difficult to determine without adequate motion compensation. Furthermore, when an access tool, needle or biopsy tool is deployed from the catheter, it may deflect due to tissue physiology or geometry, catheter bending, or the respiratory cycle airway movement.

To address this issue, the present disclosure is directed to devices, systems, methods, and computer-readable media of assessing the ability of a tool to reach and interact with the region of interest located within or outside of an airway, or to which access is otherwise limited, during the respiratory cycle. From a location inside of the airway, a clinician is able to identify optimal locations from which to achieve access to a region of interest during each peak inhalation and peak exhalation, of the respiratory cycle.

SUMMARY

Provided in accordance with the present disclosure are devices, systems, methods, and computer-readable media for navigating to a region of interest within or outside of an airway, or to which access is otherwise limited during the respiratory cycle.

According to one aspect, a system for navigating to and interacting with a region of interest during a respiratory cycle is provided. The system includes an extended working channel defining a lumen extending therethrough for receiving a tool, a computing device including a memory and at least one processor, a plurality of images stored in the memory; a display device that displays a user interface. The at least one processor configured to determine movement of the tool during the respiratory cycle of a patient obtain one of more patient health metrics from a database, and determine likely movement of airways and region of interest during the respiratory cycle of the patient based on determined movement of tool and obtained one or more patient health metrics. A program is stored in the memory that, when executed by the at least one processor, presents the user interface The user interface includes at least one image of the plurality of images depicting the region of interest and a progression of the extended working channel through the airways and a probability diagnostic and/or treatment zone defining a probable distribution of a trajectory of the tool once deployed beyond an opening of the extended working channel displayed in the at least one image based on likely movement of airways and region of interest during respiratory cycle. In another aspect, the respiratory cycle is divided into inhalation and exhalation and each image of the plurality of images stored in the memory is composed of an inhalation image, and an exhalation image.

In a further aspect, the user interface is configured to depict movement of the region of interest, extended working channel, and the airways during the respiratory cycle. In another aspect, the user interface is configured to allow a user to position the probability diagnostic and/or treatment zone in a location and determine a position of the probability diagnostic and/or treatment zone at peak inhalation and at peak exhalation so that at least a portion of the region of interest is encompassed by the probability diagnostic and/or treatment zone. In one embodiment, the user interface is further configured to display the probability diagnostic/ treatment zone with a first indicator, a second indicator, and a third indicator, where the first indicator includes a status of a range of the tool with respect to the region of interest, the second indicator includes a status of an orientation of the tool with respect to the region of interest, and the third indicator includes a status of the respiratory cycle, when the portion of the region of interest is encompassed by the probability diagnostic and/or treatment zone, the status of the second indicator changes indicate that a location of the tool allows the tool to interact with the region of interest.

In another embodiment, when the range from the opening of the extended working channel to the region of interest is less than a maximum deployable range of the tool, the status of the first indicator changes to indicate that the range of the tool allows the tool to interact with the region of interest. In a further embodiment, when both the first indicator and the second indicator indicate that orientation and range of the tool allows the tool to interact with the region of interest, the status of the third indicator changes to indicate that at either peak inhalation or peak exhalation the tool will interact with the region of interest. In a further embodiment, the user interface is further configured to allow a user to display the probability diagnostic and/or treatment zone as a three-dimensional volumetric shape.

In another embodiment, the user interface is configured such that an increase in a region of interest volume inside the probability diagnostic and/or treatment zone indicates an increase in probability that the tool will interact with a portion of the region of interest inside the probability diagnostic and/or treatment zone. In another aspect, the tool is selected from the group consisting of a needle, an access tool, a biopsy tool, a therapeutic material application tool, and an ablation tool. In a further aspect, the user interface is further configured to adjust the probability diagnostic and/or treatment zone based on the tool selected.

In another aspect, the movement of the region of interest and the airways is asynchronous during inhalation and exhalation and depicted by changes of the probability diagnostic and/or treatment zone. In a further aspect, the user interface is configured such that a length of the probability diagnostic and/or treatment zone from the opening of the extended working channel corresponds to a maximum effective range the tool can be deployed beyond the opening of the extended working channel. In another embodiment, the user interface is further configured to allow the user to display the probability diagnostic and/or treatment zone as a two-dimensional shape.

According to another aspect, a method for navigating to and determining likelihood of interacting with a region of interest during a respiratory cycle is provided. The method includes importing CT image data of a patient, generating a 3D reconstruction from the CT image data, navigating a tool to the region of interest, measuring movement of the tool during respiratory cycle of patient, obtaining one or more patient health metrics from a database. The user interface includes at least one image depicting a progression of an extended working channel having a lumen extending therethrough for receiving the tool to interact with the region of interest during the respiratory cycle, wherein the progression of the extended working channel is depicted within the 3D reconstruction and a probability diagnostic and/or treatment zone defining a probable distribution of a trajectory of the tool once deployed beyond an opening of the extended working channel based on likely movement of airways and region of interest during respiratory cycle. The method further includes displaying the user interface. Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

Figure 1:
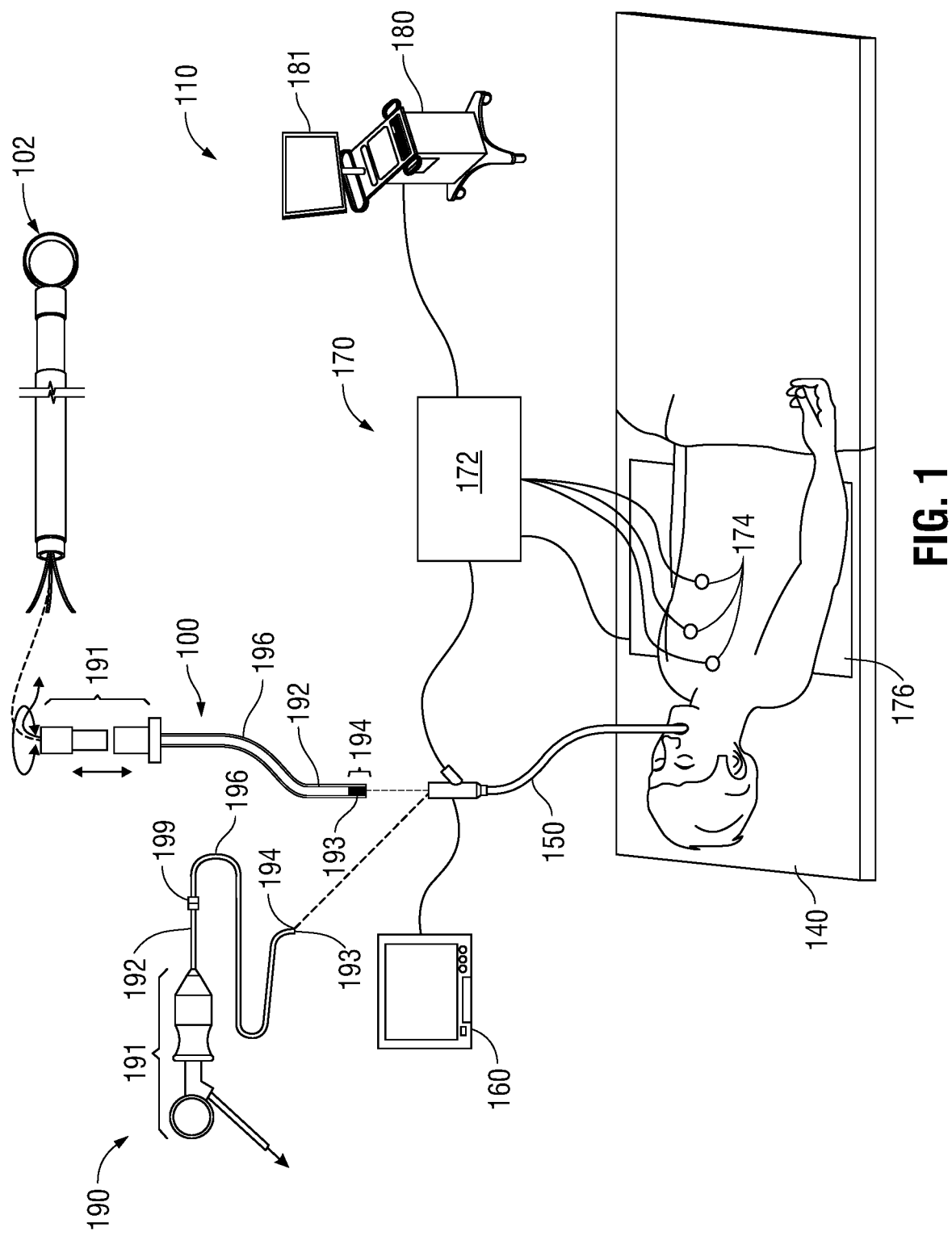
FIG. 1 is a perspective view of an electromagnetic navigation system in accordance with the present disclosure.

The present disclosure is directed to a system and method of determining and displaying proximity to a region of interest which may changes size, shape and location during the respiratory cycle, and presenting a graphical display of an area a biopsy tool, or other surgical tool, might traverse if extended from an extended working channel in the direction of the region of interest. During the respiratory cycle of a patient, airway regions expand, contract, and change location. While navigating to a lesion or diseased region of the airway, movement of the patient's airways cause access to the lesion or diseased region to change based on which peak of the respiratory cycle access is attempted. With such a system, a clinician can determine whether a change of position is desirable or necessary prior to extracting a biopsy or treating the targeted tissue. In addition, such a system allows a clinician to determine, during each peak of the respiratory cycle, based on the location, size, and shape of region of interest and the size and deformation of the biopsy tool or medication dispersal area (in the case of a therapeutic medication tool), the optimal timing for taking an biopsy or releasing therapeutic medication. Thus, the graphical display of this system grants a clinician increased confidence that a biopsy taken of or treatment administered to a region of interest has been completed with respect to the region of interest and not tissue merely in the proximity of the region of interest.

As used herein, peak inhalation refers to the peak or near-peak expansion of the patient's chest cavity as the lungs fill with air, while peak exhalation refers to the peak or near-peak expiration of air from the patient's lungs. Each of peak inhalation and peak exhalation refer to the maximum inhalation and exhalation, respectively, of patient breathing, where normal tidal volume breathing exists between peak inhalation and peak exhalation. Thus, by using the position of sensors and knowing the locations during peak inhalation and peak exhalation, which are the maximums, the locations between during normal tidal volume breathing can be determined.

An electromagnetic navigation or EMN procedure generally involves at least two phases: (1) planning a pathway to a target located within, or adjacent to, the patient's airways; and (2) navigating a probe to the region of interest along the planned pathway. These phases are generally referred to as (1) "planning" and (2) "navigation." The planning phase of an EMN procedure is more fully described in commonly owned U.S. Patent Publication Nos. 2014/0270441, 20140281961, and 2014/0282216, all entitled "PATHWAY PLANNING SYSTEM AND METHOD," filed on Mar. 15, 2013, by Baker, the entire contents of which are hereby incorporated by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB™ procedure.

With reference to FIG. 1, an EMN system 110 is provided in accordance with the present disclosure. One such ENM system is the ENB™ system currently sold by Medtronic. Among other tasks that may be performed using EMN system 110 are planning a pathway to the region of interest, navigating a positioning assembly to the region of interest, navigating a biopsy tool to the region of interest to obtain a tissue sample from the region of interest using the biopsy tool, and digitally marking the location where the tissue sample was obtained, and placing one or more echogenic markers at or around the target.

EMN system 110 generally includes an operating table 140 configured to support a patient; a bronchoscope 150 configured for insertion through the patient's mouth and/or nose into the patient's airways; monitoring equipment 160 coupled to bronchoscope 150 for displaying video images received from bronchoscope 150; a tracking system 170 including a tracking module 172, a plurality of reference sensors 174, an electromagnetic field generator 176; and a workstation 180 including software and/or hardware used to facilitate pathway planning, identification of the region of interest, navigation to the region of interest, and digitally marking the biopsy location.

FIG. 1 also depicts two types of catheter guide assemblies 100, 190. Both catheter guide assemblies 100, 190 are usable with EMN system 110 and share a number of common components. Each catheter guide assembly 100, 190 include a handle 191, which is connected to an extended working channel (EWC) 196. EWC 196 is sized for placement into the working channel of a bronchoscope 150. In operation, a locatable guide 192, including an electromagnetic (EM) sensor 194, is inserted into EWC 196 and locked into position such that EM sensor 194 extends a desired distance beyond distal tip 193 of EWC 196. The location of the EM sensor 194, and therefore distal tip 193 of EWC 196, within an electromagnetic field generated by the electromagnetic field generator 176, can be derived by the tracking module 172, and the workstation 180. Thus, EM sensor 194 and tracking module 172, in conjunction with electromagnetic field generator 176, may be used to define a volume of the patient's airways and chest volume. In addition to defining the volume of the patient's airways and chest volume, EM sensor 194 and tracking module 172, in conjunction with electromagnetic field generator 176, may also be used to determine the location of objects within the volume of the patient's airways and chest volume based on the triangulated positions of EM sensor 194. Catheter guide assemblies 100, 190 have different operating mechanisms, but the handle 191 can be manipulated by rotation and compression to steer locatable guide 192 inserted into EWC 196. Catheter guide assembly 190 is currently marketed and sold by Covidien LP under the name SUPERDIMENSION® Procedure Kits, similarly catheter guide assembly 100 is currently sold by Covidien LP under the name EDGE™ Procedure Kits, both kits include the 191, extended working channel 196, and locatable guide 192. For a more detailed description of the catheter guide assemblies 100, 190, reference is made to commonly owned U.S. Patent Publication No. 2014/0046315 filed on Mar. 15, 2013 by Ladtkow et al., the entire contents of which are hereby incorporated by reference.

As illustrated in FIG. 1, the patient is shown lying on operating table 140 with bronchoscope 150 inserted through the patient's mouth and into the patient's airways. Bronchoscope 150 includes a source of illumination and a video imaging system (not explicitly shown) and is coupled to monitoring equipment 160, e.g., a video display, for displaying the video images received from the video imaging system of bronchoscope 150.

Catheter guide assemblies 100, 190 including locatable guide 192 and EWC 196 are configured for insertion through a working channel of bronchoscope 150 into the patient's airways (although the catheter guide assemblies 100, 190 may alternatively be used without bronchoscope 150). Locatable guide 192 and EWC 196 are selectively lockable relative to one another via a locking mechanism 199. A six degrees-of-freedom electromagnetic tracking system 170 (e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system), is utilized for performing navigation, although other configurations are also contemplated. Tracking system 170 is configured for use with catheter guide assemblies 100, 190 to track the position of the EM sensor 194 as it moves in conjunction with EWC 196 through the airways of the patient, as detailed below.

As further shown in FIG. 1, electromagnetic field generator 176 is positioned beneath the patient. Electromagnetic field generator 176 and the plurality of reference sensors 174 are interconnected with tracking module 172, which derives the location of each reference sensor 174 in six degrees of freedom. One or more of reference sensors 174 are attached to the chest of the patient. The six degrees of freedom coordinates of reference sensors 174 are sent to workstation 180, which includes application 181 where data from sensors 174 is used to calculate a patient coordinate frame of reference.

In one embodiment of the present disclosure, reference sensors 174 may be placed on the patient's chest during a pre-procedure CT scan while the patient does a full or partial breath hold during the CT scan, and/or on the patient's chest during the procedure. During the procedure, the same or similar reference sensors 174 or CT compatible surrogates may be attached to the chest of the patient. By utilizing the locations of reference sensors 174 within the electromagnetic field generated by electromagnetic field generator 176 and comparing them to the location of the reference sensors in the pre-procedure CT scan, a determination of minimum and maximum chest locations may be determined. The location of reference sensors 174 obtained during the pre-procedure CT scan are typically taken at either full inhalation or full exhalation of the patient and identify the patient's maximum inhalation or maximum exhalation of the respiratory cycle. By comparing the movement and locations of reference sensors 174 during the procedure to the locations of the reference sensors 174 during the pre-procedure CT scan and determining differences, between the detected location, either the minimum and maximum of the respiratory cycle may be ascertained and ultimately used to determine movement of a target during the respiratory cycle as will be explained in greater detail below.

In an alternative embodiment, reference sensors 174 are not placed on the chest of the patient during the pre-procedure CT scan. Instead, in the pre-procedure CT scan landmarks on the chest wall such as ribs are identified and while preparing for the procedure reference sensors 174 may be placed proximate those landmarks on the patient while in electromagnetic field generated by electromagnetic field generator 176. Next, the patient is requested to take a deep breath with the reference sensors 174 in place, and subsequently instructed to breathe normally. The sensed location of reference sensors 174 placed over the landmarks identified in the pre-procedure CT scan (at full breath hold) mimics the location of the landmarks in the pre-procedure CT scan. This sensed location at full breath hold can be utilized as above as a maximum (or minimum) and the differences, between the detected location of reference sensors 174 during normal breath and either the minimum and maximum of the respiratory cycle may be used to determine movement of a target during the respiratory cycle.

Still further, in another embodiment no direct comparison is made to the CT scan and while setting up for a procedure, reference sensors 174 are place on the patient's chest and the locations and/or movement of reference sensors 174 are monitored and stored. As the patient respires during the procedure, a determination is made of the maximum and minimum locations of the chest based on the locations of reference sensors 174 within the electromagnetic field generated by electromagnetic field generator 176. By utilizing this location information, a determination of the patient's peak inhalation or peak exhalation of the respiratory cycle may be made, and used to determine movement of a target during the respiratory cycle.+ In some embodiments, the maximum inhalations and maximum exhalations are relative to prior movement of reference sensors 174.

Further shown in FIG. 1 is a catheter endobronchial tool 102 that is insertable into catheter guide assemblies 100, 190 following navigation to a target and removal of locatable guide 192. Endobronchial tool 102 is configured to collect one or more tissue sample from the region of interest. As detailed below, endobronchial tool 102 is further configured for use in conjunction with tracking system 170 to facilitate navigation of endobronchial tool 102 to the region of interest, tracking of a location of endobronchial tool 102 as it is manipulated relative to the region of interest to obtain the tissue sample, and/or marking the location where the tissue sample was obtained. During navigation, EM sensor 194, in conjunction with tracking system 170, enables tracking of EM sensor 194 and/or endobronchial tool 102 as EM sensor 194 or endobronchial tool 102 is advanced through the patient's airways.

Although navigation is detailed above with respect to EM sensor 194 being included in locatable guide 192 it is also envisioned that EM sensor 194 may be embedded or incorporated within endobronchial tool 102 where endobronchial tool 102 may alternatively be utilized for navigation without need of locatable guide 192 or the necessary tool exchanges that use of locatable guide 192 requires. A variety of useable biopsy tools are described in Patent Publication No. US 2015/0141809 A1 and entitled DEVICES, SYSTEMS, AND METHODS FOR NAVIGATING A BIOPSY TOOL TO A TARGET LOCATION AND OBTAINING A TISSUE SAMPLE USING THE SAME, filed Sep. 17, 2014 and Patent Publication No. US 2015/0265257 A1 having the same title and filed Dec. 9, 2014, the entire contents of each of which are incorporated herein by reference and useable with EMN system 110 as described herein.

Generally, during imaging, the patient's breath is held during the CT scan thereby creating a single set of image slices (CT image data) based on either the peak inhalation or peak exhalation of the respiratory cycle. During procedure planning, workstation 180 utilizes CT image data, or other image data in DICOM format, for generating and viewing a three-dimensional model ("3D model") of the patient's airways. The 3D model and image data derived from the 3D model enables the identification of the region of interest (automatically, semi-automatically or manually), and allows for the selection of a pathway through the patient's airways to the region of interest. More specifically, the CT scans are processed and assembled into a 3D volume, which is then utilized to generate the 3D model of the patient's airways. The 3D model may be presented on a display monitor 181 associated with workstation 180, or in any other suitable fashion. Using workstation 180, various slices of the 3D volume and views of the 3D model may be presented and/or may be manipulated by a clinician to facilitate identification of a region of interest and selection of a suitable pathway through the patient's airways to access the region of interest. The 3D model may also show marks of the locations where previous biopsies were performed, including the dates, times, and other identifying information regarding the tissue samples obtained. These marks may also be selected as the region of interest to which a pathway can be planned. Once selected, the pathway is saved for use during the navigation procedure.

Figure 2:
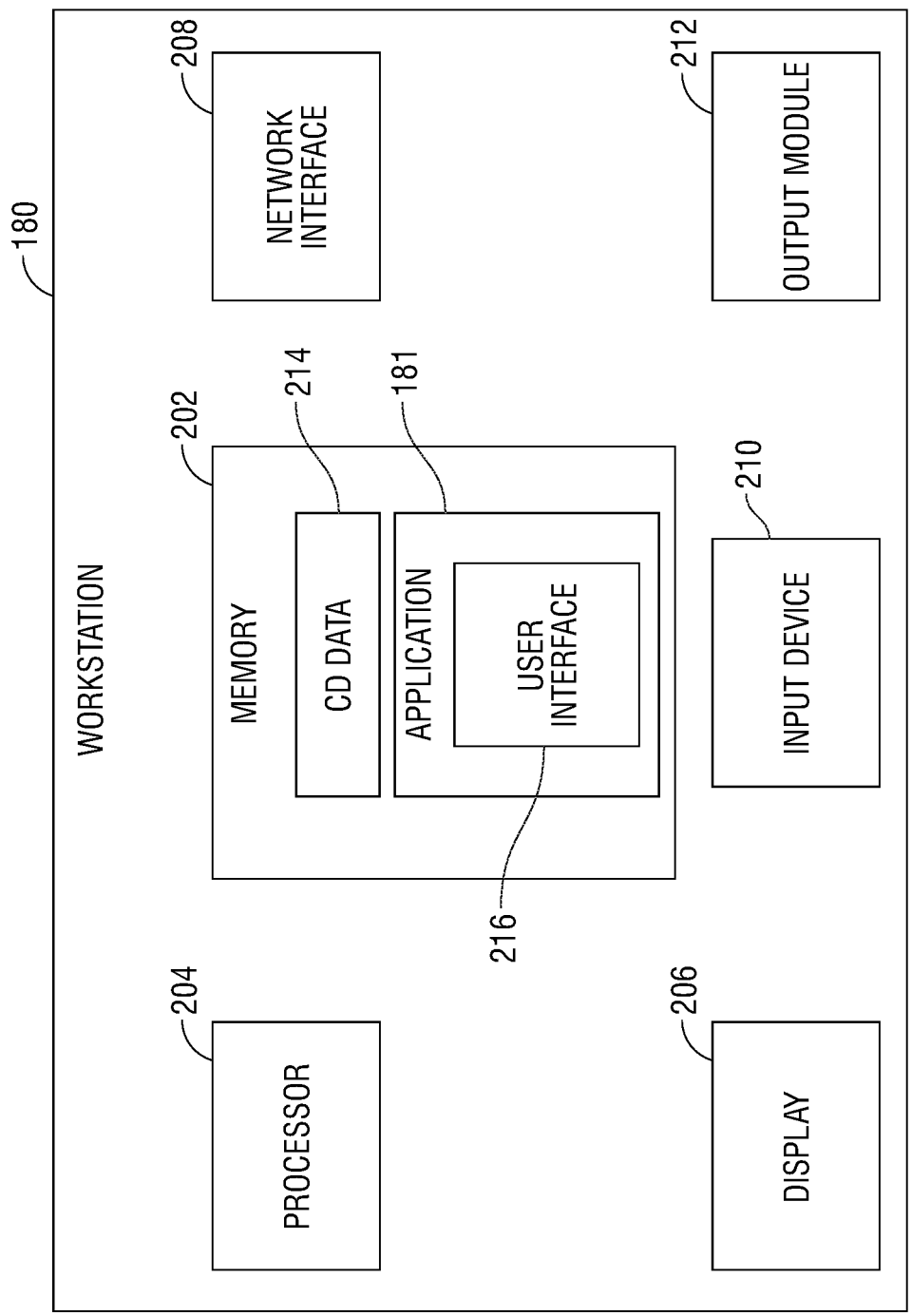
FIG. 2 is a schematic diagram of a workstation configured for use with the system of FIG. 1.

Turning now to FIG. 2, a system diagram of workstation 180 is illustrated. Workstation 180 may include memory 202, which further includes CT data 214 and application 181 including user interface 216, processor 204, display 206, network interface 208, input device 210, and/or output module 212. In addition to CT data 214, memory 202 may further include a database 203, which includes patient health metrics based on characteristics of the patient such as, age, weight, height, health risks, respiratory ailments, etc. In addition, database 203 may include patient health metrics based on sensor locations obtained during an initial CT scan. The initial CT scan of the patient is generally completed during a full breath-hold or peak inhalation of the patient. Thus, the patient health metrics based on sensor location stored in database 203 provide the locations of sensors during near-peak inhalation. Because the locations of sensors obtained during the procedure cannot exceed the full breath-hold or peak inhalation locations of sensors obtained during the initial CT scan, a comparison of the patient health metrics based on sensor locations obtained during an initial CT scan and the locations of sensors obtained during patient respiration during the procedure can be used to determine likely airway and region of interest movement during the respiration cycle. In addition, the patient health metrics may also include additional patient data such as likelihood of coughing, common vascular or cardiac pulsations, and other medical causes of movement of regions of interests within and outside of the airways and the airways based on patient medical history. By using the patient health metrics in database 203, a prediction may be made to determine likely airway and region of interest movement during the procedure.

Thus, the 3D volume is created based on CT data 214 and based on the health metrics, probable movement of the 3D volume during respiration can be determined. For example, if data for a patient indicates that the patient has a respiratory ailment, which prevents the patient from inhaling fully during inhalation, processor 204 after creation of the 3D model can determine the likely movement of the airways and region of interest during each peak of the respiratory cycle.

During respiration of the patient, EM sensor 194, in conjunction with tracking system 170, enables tracking of endobronchial tool 102 as patient breathes during a procedure. Tracking system 170 is capable of determining movement of the airways and a region of interest during respiration based on the movement of endobronchial tool 102. Movement of the airways and regions of interest is asynchronous during respiration and processor 204 using tracking information from tracking system 170 provides motion compensation for the location, size and shape of the airways and regions of interest during the respiratory cycle. Thus, although the airways and regions of interest may, during consecutive inhalation or exhalation periods of the respiratory cycle, change location, size and shape asynchronously, processor 204 determines the probable likelihood of the airways and regions of interest being located at a given location. Using information from database 203 in conjunction with tracking information from tracking system 170, probable movement of airways and region of interest is determined and used to provide the clinician with an indication of the best location and peak of respiration (inhalation or exhalation) for performing a procedure.

Although the respiratory cycle is described herein as including only an inhalation and exhalation peak, it is also understood that the respiratory cycle may be composed of additional transition points between inhalation and exhalation. In further embodiments, processor 204 may use the transition points between the inhalation and exhalation peaks to determine movement of the region of interest.

Figure 3A:
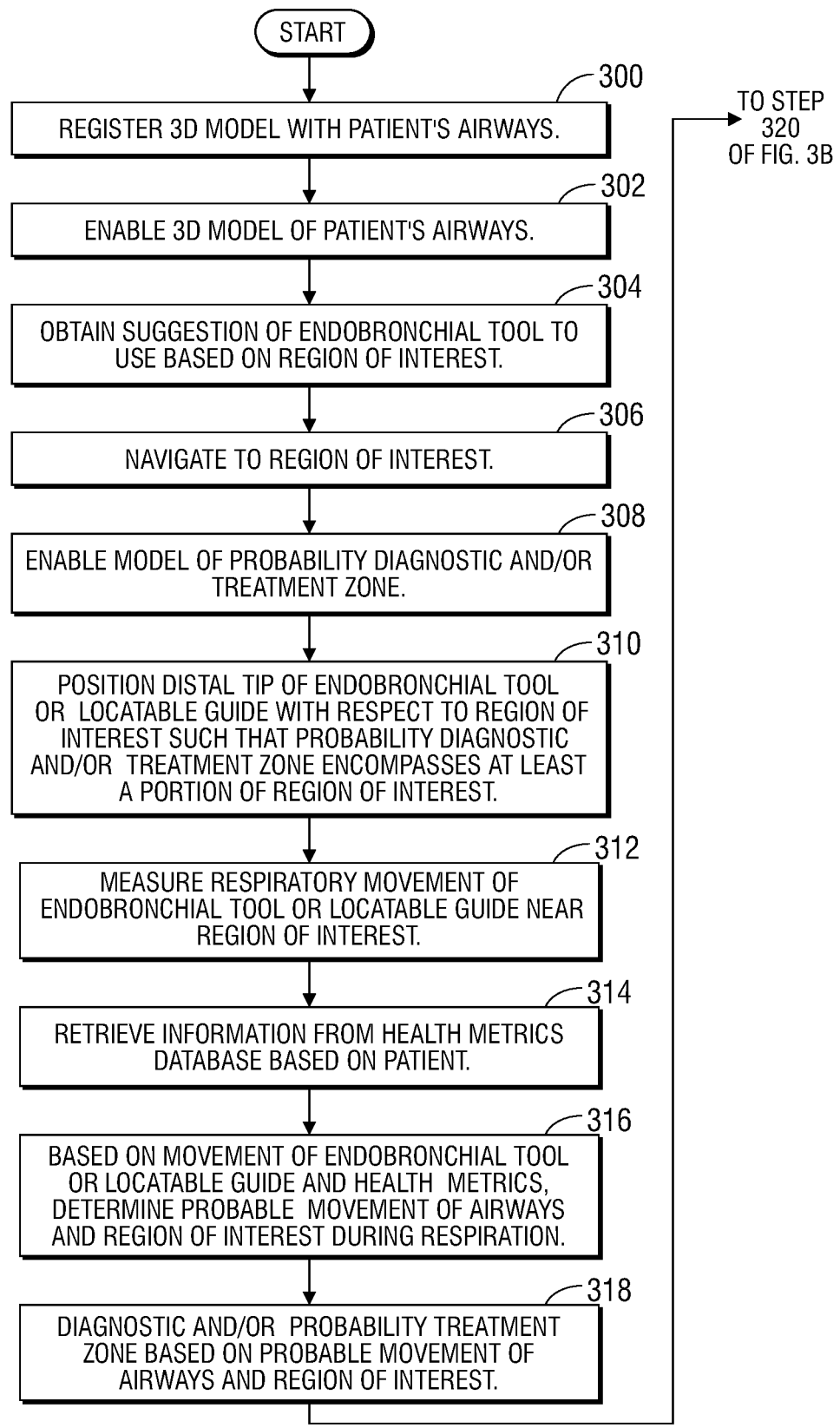
FIGS. 3A and 3B are flowcharts illustrating a method for navigating to the location of a region of interest within or outside of an airway, or to which access is otherwise limited, provided in accordance with the present disclosure.
Figure 3B:
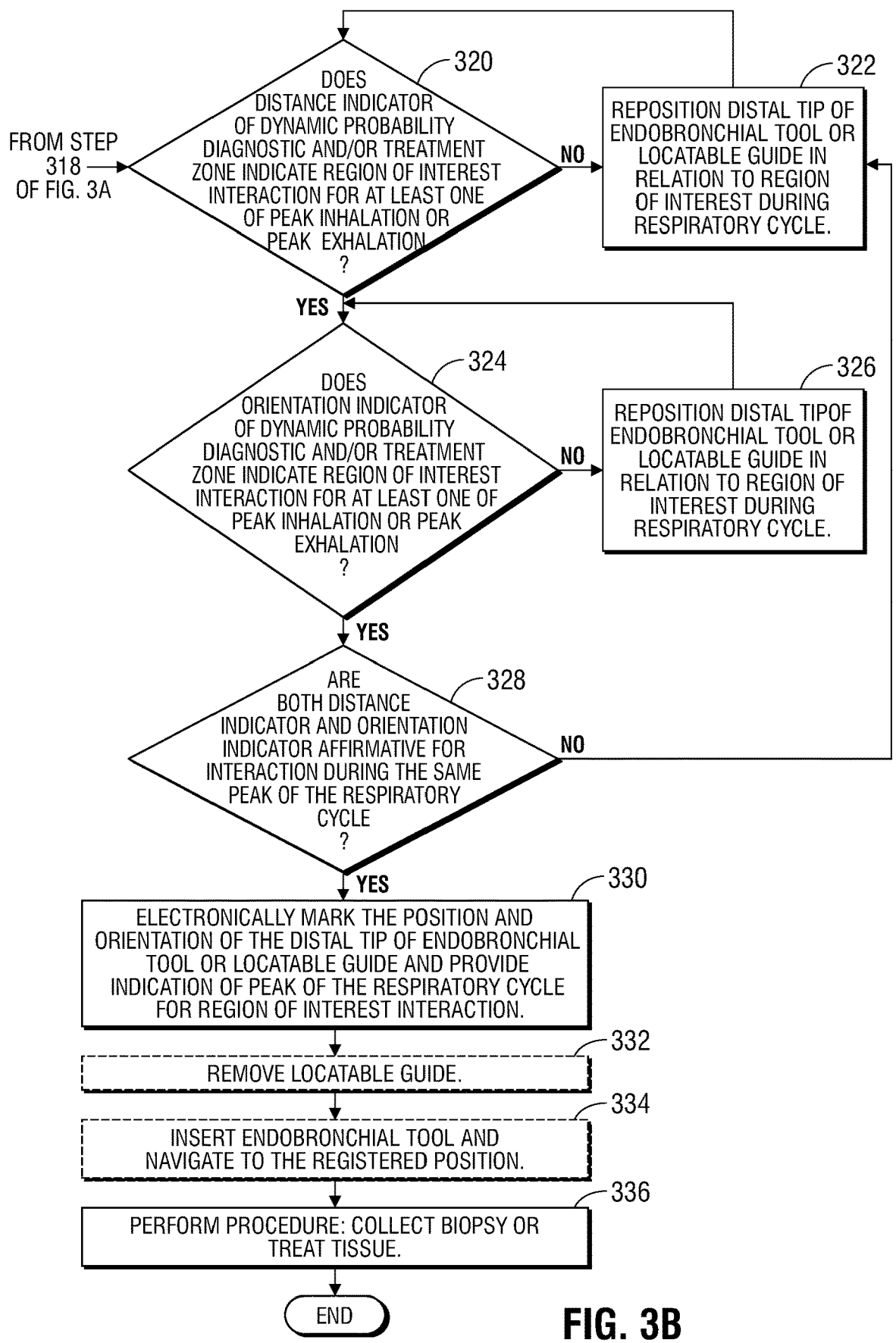

Referring now to FIGS. 3A and 3B, a flowchart of an example method for navigating to a region of interest outside of an airway, or to which access is otherwise limited, during a procedure in accordance with the present disclosure is illustrated. Prior to the start of navigation, the clinician loads a navigation plan including the 3D model of the lungs of the patient and the planned pathways to identified region of interest into a navigation application 181 from memory 202, via network interface 208, or a USB drive. An example of the navigation application can be found in commonly assigned U.S. patent application Ser. No. 14/753,288 entitled "SYSTEM AND METHOD FOR NAVIGATING WITHIN THE LUNG," filed on Jun. 29, 2015, by Brown et al., the entire contents of which are incorporated herein by reference.

To perform automatic registration, the clinician advances bronchoscope 150, locatable guide 192, and EWC 196 into each region of the patient's airways in step 300 until registration has occurred between the location of EM sensor 194 of locatable guide 192, the 3D model, and other data in the navigation plan. Details of this registration are set forth in U.S. patent application Ser. No. 14/790,581 entitled "REAL-TIME AUTOMATIC REGISTRATION FEEDBACK," filed on Jul. 2, 2015, by Brown et al., the contents of which are incorporated herein by reference. Alternative registration techniques including manual are possible and described in detail in U.S. Pat. No. 7,233,820 entitled "ENDOSCOPE STRUCTURES AND TECHNIQUES FOR NAVIGATING TO A TARGET IN BRANCHED STRUCTURE" the entire contents of which are incorporated herein by reference. Once registered, the clinician enables a virtual 3D model of the patient's airways in step 302.

Optionally, in step 304, prior to navigation of EWC 196 or locatable guide 192, processor 204 may optionally suggest to the clinician optimal endobronchial tool 102 which, based on the 3D model, are best suited for use for the procedure. In some embodiments, the clinician begins navigation with locatable guide 192, while in other embodiments, navigation is done with endobronchial tool 102.

In step 306, the clinician begins navigating to a region of interest 403 (See, FIGS. 4A and 6) following a pathway identified in navigation plan at step 300. As distal tip 193 of EWC 196, endobronchial tool 102, or locatable guide 192 approaches region of interest 403, the clinician either manually enables or the application automatically enables a display of the model of the probability diagnostic and/or treatment zone ("PTZ") 404, at step 308. As discussed further in FIG. 4A, PTZ 404 provides the clinician with three-dimensional display of a volume extending from distal tip 193 of EWC 196 or locatable guide 192, which shows where endobronchial tool 102 is capable of reaching and interacting with portions of region of interest 403 which are displayed within the volume of PTZ 404. Thus, the PTZ provides a clinician with a volume where diagnostics and/or treatment of region of interest 403 is most probable.

Once PTZ 404 is enabled, the clinician positions distal tip 193 of EWC 196, endobronchial tool 102, or locatable guide 192 with respect to region of interest 403. As the clinician, following the pathway plan, approaches region of interest 403, distal tip 193 of EWC 196, endobronchial tool 102, or locatable guide 192 may be positioned such that the display of PTZ 404 encompasses at least a portion of region of interest 403, as described in step 310. In some embodiments, the clinician has the option of disabling PTZ 404 during navigation until distal tip 193 of EWC 196, endobronchial tool 102, or locatable guide 192 has moved closer to region of interest 403, and once each is located in a position closer to region of interest 403, PTZ 404 may be re-enabled.

In step 312, EM sensor 194, in conjunction with tracking system 170, enables tracking of endobronchial tool 102 or locatable guide 192 as patient breaths to determine movement of endobronchial tool 102 or locatable guide 192. In step 314, health metrics information for the patient is obtained from database 203, which is used to determine likely movement of airways and regions of interest 403 during patient respiration. In step 316, using health metrics for the patient in conjunction with movement information of endobronchial tool 102 or locatable guide 192 from tracking system 170, processor 204 determines probable movement of airways and region of interest 403.

In step 318, using the probable movement of airways and region of interest 403, PTZ 404 is modified to dynamically include: (1) a distance indicator, which changes and provides an indication of interaction with region of interest 403 based on distance of distal tip 193 of EWC 196, endobronchial tool 102, or locatable guide 192 to region of interest 403 at peak inhalation and peak exhalation; and (2) an orientation indicator, which changes and provides an indication of likely interaction with region of interest 403 based on orientation of distal tip 193 of EWC 196, endobronchial tool 102, or locatable guide 192 with respect to region of interest 403 at peak inhalation and peak exhalation. In further embodiments, the distance indicator may also provide a counter, which decrements as distal tip 193 of EWC 196, endobronchial tool 102, or locatable guide 192 approaches region of interest 403.

As described in further detail in the description of FIGS. 4A-5C, the distance indicator and orientation indicator of PTZ 404 may include various visual, audio and/or tactile indicators, which enable the clinician to determine both the distance to region of interest 403 and the orientation of endobronchial tool 102 with respect to region of interest 403 during respiration. For example, PTZ 404 may change from red to green, or other contrasting colors, as an indication of when the location of distal tip 193 of EWC 196, endobronchial tool 102, or locatable guide 192 likely allows interaction with region of interest 403 by endobronchial tool 102 based on distance. Additionally, PTZ may provide an audio indicator, such as a beeping sound, at peak inhalation or peak exhalation thereby notifying the clinician when interaction with region of interest will likely occur.

In step 320, confirmation is made of the distance for likely interaction between endobronchial tool 102 and region of interest 403 based on location of distal tip 193 of EWC 196, endobronchial tool 102, or locatable guide 192. If, at step 320, it is confirmed that for either peak inhalation or peak exhalation endobronchial tool 102 will likely interact with region of interest 403, based on distance, the clinician proceeds to step 324 for confirmation of orientation. It is contemplated that processor 204 stores the indication of which peak of the respiratory cycle (inhalation or exhalation) endobronchial tool 102 will likely interact with region of interest 403.

If alternatively, the distance confirmation of step 320 indicates that endobronchial tool 102 will not interact with region of interest 403 at either peak inhalation or peak exhalation, the clinician is notified to reposition distal tip 193 of EWC 196, endobronchial tool 102, or locatable guide 192, at step 322. Following repositioning, the procedure returns to step 320 where another determination of whether endobronchial tool 102 will interact with region of interest 403. Although not shown in FIG. 3B, it is contemplated that if, after multiple attempts of repositioning, it is determined that endobronchial tool 102 does likely not interact with region of interest 403 the clinician may be notified to restart the procedure using a different endobronchial tool 102.

In step 324, confirmation is made of the orientation of distal tip 193 of EWC 196, endobronchial tool 102, or locatable guide 192 for likely interaction with region of interest 403. If at step 324, it is confirmed that for either peak inhalation or peak exhalation endobronchial tool 102 will likely interact with region of interest 403, based on orientation, the clinician proceeds to step 328 for confirmation of the respiratory peak for the procedure.

If alternatively, the orientation confirmation of step 324 indicates that endobronchial tool 102 will not interact with region of interest 403 at either peak inhalation or peak exhalation, the clinician is notified to reposition distal tip 193 of EWC 196, endobronchial tool 102, or locatable guide 192, at step 326. Following repositioning, the procedure returns to step 324 where another determination of whether endobronchial tool 102 will interact with region of interest 403.

At step 328, processor 204 determines whether both the distance indicator and orientation indicator indicate that endobronchial tool 102 will likely interact with region of interest 403 during the same peak of the respiratory cycle. For example, if it is determined, at step 320, that at the current location there is a high likelihood that endobronchial tool 102 will interact with region of interest 403 based on distance during the inhalation peak of the respiratory cycle and it is determined, at step 324, that at the current orientation there is a high likelihood that endobronchial tool 102 will interact with region of interest 403 based on orientation during the inhalation peak of the respiratory cycle, then the procedure will proceed to step 330 allowing the clinician to electronically mark the position and orientation of endobronchial tool 102 or locatable guide 192 and provide the clinician with an indication that based on current location and orientation, endobronchial tool 102, will likely interact with region of interest 403 during the inhalation peak of the respiratory cycle.

If, at step 328, it is determined that the distance indicator and orientation indicator indicate that interaction with region of interest 403 will occur for different periods of the respiratory cycle (i.e., distance interaction only during the exhalation peak and orientation interaction only during the inhalation peak), the procedure returns to step 322 and the clinician is notified to reposition distal tip 193 of EWC 196, endobronchial tool 102, or locatable guide 192.

Locatable guide 192 (if used) may be optionally removed at step 332 and endobronchial tool 102 which was optimally suggested in step 304 may be inserted through EWC 196 to the electronically marked position, at step 334.

At step 336, using the electronically marked position and orientation, and the provided indication of which peak of respiration interaction with region of interest 403 is likely to occur, the clinician may collect a biopsy or treat tissue.

In further embodiments, following treatment or biopsy of region of interest 403, processor 204 may also provide a post-treatment overlay, which provides a clinician with a display of region of 403 that shows the volume of region of interest 403 which has been affected by endobronchial tool 102. This post-treatment overlay will enable a clinician to determine the affected volume of region of interest 403 and may suggest areas, which require additional treatment.

Figure 4A:
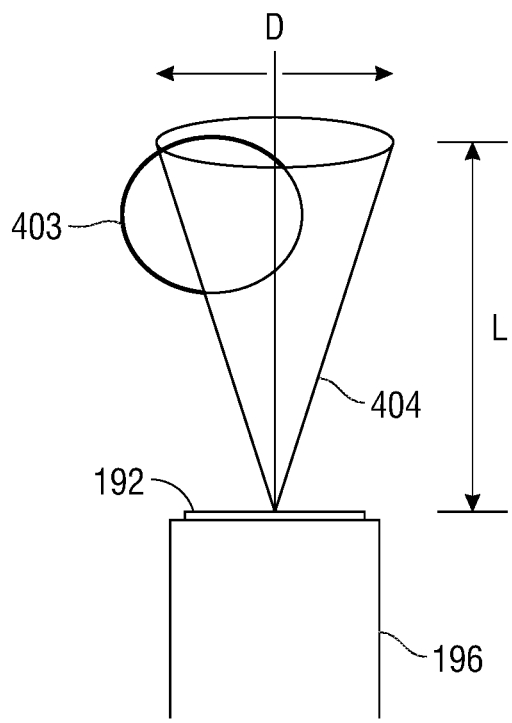
FIG. 4A is an illustration of a probability diagnostic and/or treatment zone and region of interest displayed as a three-dimensional shape at peak inhalation.

Referring now to FIG. 4A, PTZ 404 is depicted as a three-dimensional volumetric shape displayed during, for example, the inhalation peak of the respiratory cycle. In this instance, PTZ is depicted by a cone shaped projection emanating from the center point of distal tip 193 of EWC 196. The cone length L indicates the maximum useful or effective distance a tool (e.g., a biopsy tool, a microwave or radiation ablation tool, a chemotherapy tool, a therapeutic medication application tool, a brachytherapy tool, a marker placement tool, or other similar laparoscopic tools) can extend beyond distal tip 193 of EWC 196. The cone diameter D indicates the maximum probable distribution or deflection of a tool when extended beyond EWC 196. As will be appreciated by those of skill in the art, the maximum length for which the tool is useful or effective may vary depending on the tool employed, and a selection feature may be enabled on the user interface of the navigation application to vary the length of the cone. Although shown as a conical overlay deploying beyond EWC 192 opening, PTZ 404 may be configured to have various shapes depending on physical attributes of the tool being employed.

Figure 4B:
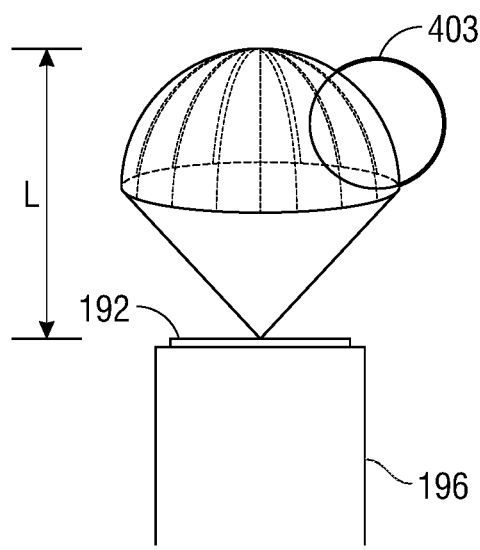
FIG. 4B is an illustration of a probability diagnostic and/or treatment zone for therapeutic medication dispersal and region of interest as a three-dimensional shape at peak inhalation.

In other embodiments, as shown in FIG. 4B, PTZ 404 may be depicted as a three-dimensional volumetric cone shaped projection with a spherical cap emanating from the center point of distal tip 193 of EWC 196. This embodiment details the use of a therapeutic medication application tool. A cone shaped projection with a spherical cap (or other applicable shape) indicates the maximum probable distribution of a therapeutic medication, which is distributed beyond distal tip 193 of EWC 196. Although the therapeutic medication may continue to be distributed beyond the volumetric shape shown in FIG. 4B the volumetric shape details the maximum volume for which the therapeutic medication is useful or effective. In each instance, the shape and volume of PTZ 404 is based on the type of tool, type of therapeutic medication, composition of surrounding tissue, or other characteristic, which may affect the volume which a tool or medication may reach once deployed beyond distal tip 193 of EWC 196.

As illustrated by FIGS. 4A and 4B, at peak inhalation PTZ 404 is displayed as partially encompassing region of interest 403 indicating that at peak inhalation endobronchial tool 102 extending from distal tip 193 of EWC 196 is capable of likely interacting with region of interest 403 at the encompassed areas.

Figure 4C:
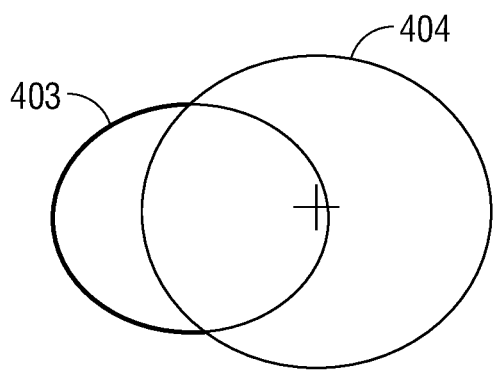
FIG. 4C is an illustration of a probability diagnostic and/or treatment zone and region of interest displayed as a three-dimensional shape at peak inhalation corresponding to FIG. 4A.
Figure 4D:
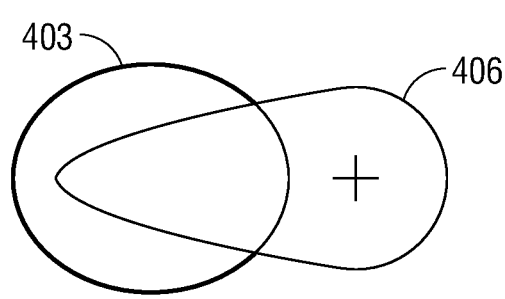
FIG. 4D is an illustration of a probability diagnostic and/or treatment zone and region of interest displayed as a three-dimensional shape at peak inhalation corresponding to FIG. 4A.

Turning now to FIGS. 4C and 4D, a comparison is shown of two-dimensional overlaid projections viewed from EWC 196 during the inhalation peak of the respiratory cycle as a circle corresponding to the cone PTZ 404 of FIG. 4A and an unbalanced ellipsoid 406. As illustrated in FIG. 4C, at peak inhalation region of interest 403 is partially encompassed by PTZ 404. In other instances, a tool may exit distal tip 193 of EWC 196 and become deflected by tissue. As will be appreciated by those of skill in the art the unbalanced ellipsoid may represent the deflection of a tool, which flexes in one direction more than in others. For example, if tissue or nearby material has a composition which will impedes the movement of endobronchial tool 102 following deployment, the two-dimensional overlaid projection, as view from distal tip 193 of EWC 196, will become extended illustrating the likely deflection of endobronchial tool 102.

Figure 5A:
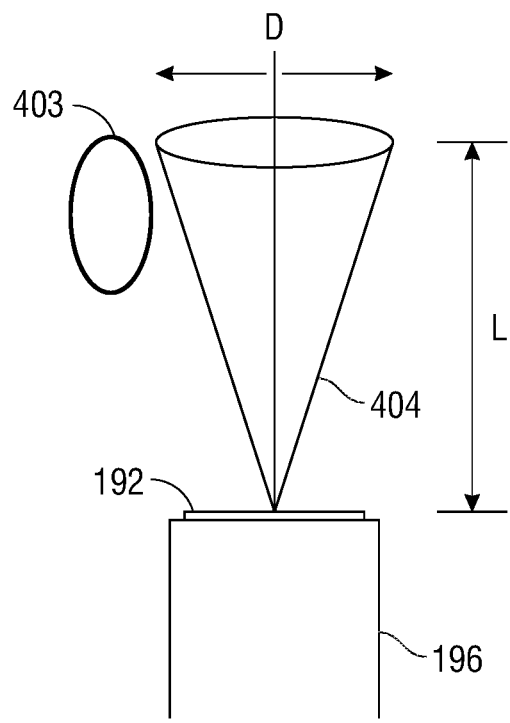
FIG. 5A is an illustration of a probability diagnostic and/or treatment zone and region of interest displayed as a three-dimensional shape at peak exhalation.
Figure 5B:
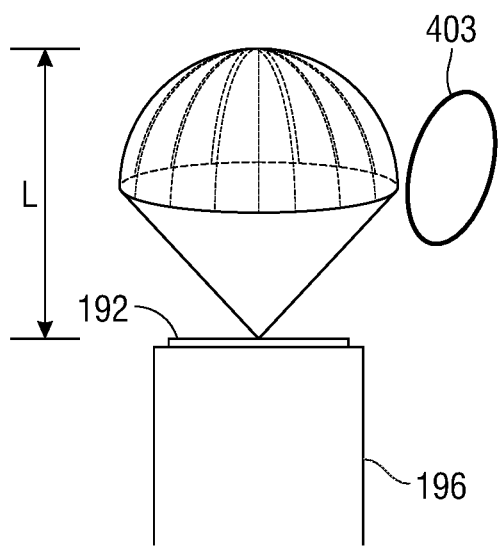
FIG. 5B is an illustration of a probability diagnostic and/or treatment zone for therapeutic medication dispersal and region of interest as a three-dimensional shape at peak exhalation.

FIGS. 5A, 5B, 5C, and 5D illustrate region of interest 403 and PTZ 404 at peak exhalation of the respiratory cycle. As shown in FIGS. 5A and 5B, at peak exhalation, PTZ 404 is altered in its location and region of interest 403 has become compressed and is located out of range of PTZ 404. At peak exhalation, due to movement of the airways and region of interest 403, the current orientation and position of endobronchial tool 102 is not capable of interacting with region of interest 403. FIGS. 5A and 5B illustrate a PTZ 404, which may be deflected due to changes in positioning of the airway wall during exhalation, while region of interest 403 may become elongated and compressed. In each instance, PTZ 404 is unable to interact with region of interest 403 during the exhalation peak of the respiratory cycle and from this it can be determined that endobronchial tool 102 is not capable of interacting with region of interest 403.

Figure 5C:
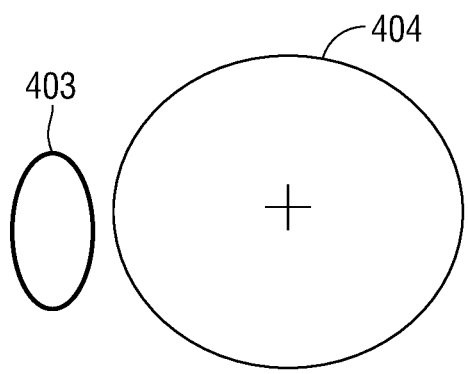
FIG. 5C is an illustration of a probability diagnostic and/or treatment zone and region of interest displayed as a three-dimensional shape at peak exhalation corresponding to FIG. 5A.
Figure 5D:
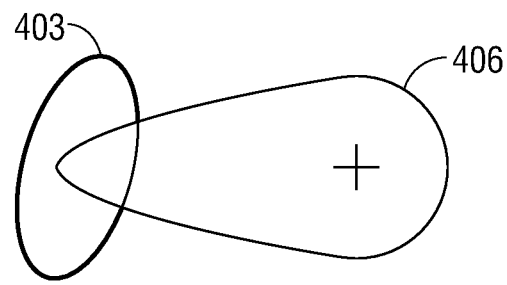
FIG. 5D is an illustration of a probability diagnostic and/or treatment zone and region of interest displayed as a three-dimensional shape at peak exhalation corresponding to FIG. 5A.

Turning now to FIGS. 5C and 5D, a comparison of two-dimensional overlaid projections viewed from EWC 196 during the exhalation peak of the respiratory cycle, similar to FIG. 4C for inhalation. As illustrated in FIG. 5C, during the exhalation peak of the respiratory cycle endobronchial tool 102 is unable to interact with region of interest 403 and as illustrated in FIG. 5D, is only partially able to affect region of interest 403.

In addition to PTZ 404, FIGS. 4A, 4B, 5A, and 5B each illustrate region of interest 403 as a three-dimensional volumetric shape, which is based on characteristics of region of interest 403 (i.e., size, shape, tissue type, and density). At peak inhalation and peak exhalation of the respiratory cycle, the location, size, and shape of region of interest 403 and endobronchial tool 102 may change in an asynchronous manner based on the characteristics of region of interest 403 and the surrounding tissue. As described with regard to FIG. 2, database 203 includes health metrics for region of interest 403. Using database 203, the likelihood of movement, compression or expansion of region of interest 403 at peak inhalation and peak exhalation of the respiratory cycle may be determined. For example, for a less dense region of interest 403 with a more malleable tissue type, region of interest 403 may move a greater distance from its initial location at peak exhalation and may compress to a smaller volume. In other examples, and dependent on other characteristics of region of interest 403, at peak inhalation region of interest 403 may increase in size and shape while remaining in its initial location. In each instance, the distance and orientation indicators of PTZ 404 provide the clinician with the likelihood of interaction of with region of interest 403 during the respiratory cycle. Although FIGS. 4A and 4B depicts region of interest 403 as being partially encompassed by PTZ 404 at peak inhalation and FIGS. 5A and 5B depicts region of interest 403 as being unencompassed by PTZ 404 at peak exhalation, based on the type of endobronchial tool 102 and composition of region of interest 403 and surrounding tissue, the shapes and interactions of PTZ 404 with region of interest 403 may change.

In a further embodiment, PTZ 404 may have different colors, and may change color as more of region of interest 403 is within PTZ 404. Thus, the clinician is provided feedback regarding the sufficiency of the coverage of region of interest 403, within PTZ 404, and can have greater confidence of reaching region of interest 403 as PTZ 404 changes from a red color indicating too little or no region of interest 403 in PTZ 404, to blue indicating that greater than some threshold portion of region of interest 403 is within PTZ 404.

Additionally, PTZ 404 may contain various indicators, which enable the clinician to determine both the distance to region of interest 403 and the orientation of endobronchial tool 102 with respect to region of interest 403. For example, as PTZ 404 is manipulated to a view as shown in FIG. 4C, statuses of indicators may change to ensure that the distance L (shown in FIG. 4A) is better understood. Once the distance L is greater than the distance from distal tip 193 of EWC 196 to region of interest 403, the status of the distance indicator changes to notify the clinician that region of interest 403 is within PTZ 404.

Figure 6:
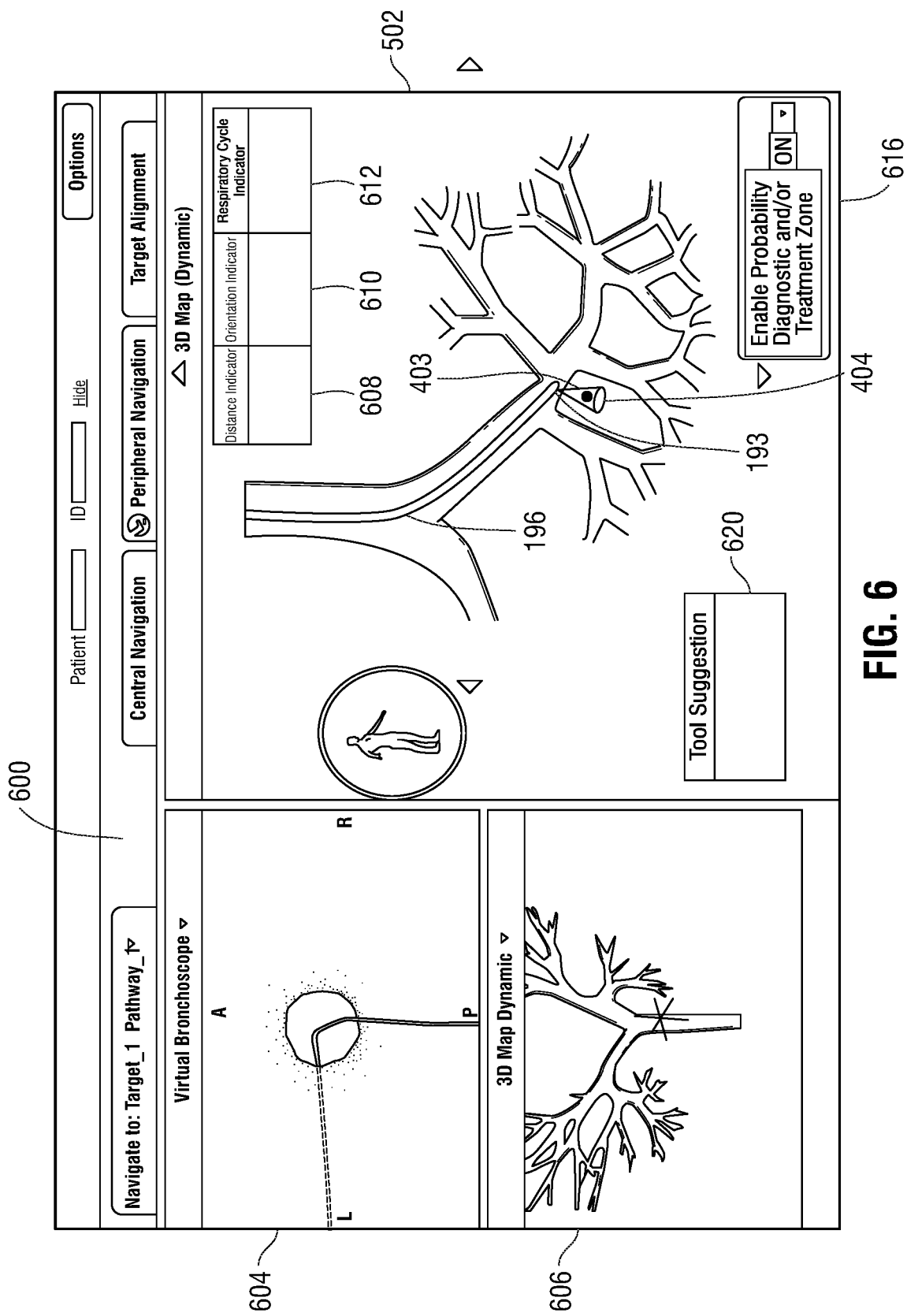
FIG. 6 is an illustration of a user interface of the workstation of FIG. 1 and FIG. 2 presenting multiple views of 3D models for navigating to a region of interest location in accordance with the present disclosure.

As shown in FIG. 6, in accordance with embodiments of the present disclosure, once registration is complete, display 181 presents user interface 600 to the clinician with a number of views 602, 604, and 606, to assist the clinician in navigating locatable guide 192 and EWC 196 to region of interest 403. User interface 600 may include a local view (3D map static) 602, a virtual bronchoscope view 604, and a 3D map dynamic view 606. Local view 602 also presents the clinician with a visualization of distal tip 193 of EWC 196 and EM sensor 194 of locatable guide 192. Other views may be presented without departing from the scope of the present disclosure. As EWC 196 and locatable guide 192 advance, each of the views 602, 604, and 606 is updated to account for the change in location.

PTZ 404 may be a graphic overlay applied by the navigation application when distal tip 193 of EWC 196 is in proximity of region of interest 403. PTZ 404 may be presented in any of the views depicted on user interface 600 to assist in the final orientation of EWC 196. As noted above, the user interface 600 may include a user activated "Enable Probability Diagnostic and/or Treatment Zone" button 616 allowing the clinician to display the 404 PTZ in any view depicted on the user interface 600. In some embodiments, this may be particularly useful in 3D viewing modes such the 3D map view 606 and/or virtual bronchoscopy view 604.

User interface 600 may additional include distance indicator 608, orientation indicator 610, and respiratory cycle indicator 612 which provide feedback on distance to region of interest 403, orientation with respect to region of interest 403, and sufficient access to region of interest 403 during each peak of the respiratory cycle. In one embodiment, indicators 608, 610, 612 may alternate between two colors or two shapes depending on the distance and orientation. For example, and as stated herein, when the distance to region of interest 403 from distal tip 193 of EWC 196 is within the distance of interaction for endobronchial tool 102, distance indicator 608 may change color from red to green or change from an "X" to a check mark as an indicator that from the current location to region of interest 403, endobronchial tool 102 is capable of interacting. In addition, orientation indicator 610 may change based on the orientation of endobronchial tool 102 with respect to region of interest 403 and the adequacy of endobronchial tool 102 interacting with region of interest 403. Respiratory cycle indicator 612 may provide an audio beep to the clinician indicating during which peak of respiration interaction with region of interest 403 is likely to occur.

In further embodiments, user interface 600 may include a tool suggestion window 620. During the respiratory cycle, processor 204, using a tracking system 170, may analyze the movement of the airways during both inhalation and exhalation and based on the movement of the airway and the movement of region of interest 403. User interface 600 may provide with suggestion interface window 620, a specific endobronchial tool 102 or tools, which are useful based on the movement during respiratory cycle, tissue type to be obtained, the specific procedure, and other characteristics that may be affected by the respiratory cycle. In further embodiments, user interface 600 may also provide a display of a confidence rating of interacting with region of interest 403 detailing percentage likelihood for interacting with region of interest 403.

Referring back to the computer-readable media of FIG. 2, memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 180.

Further aspects of the system and method are described in co-pending and commonly-owned U.S. patent application Ser. No. 14/790,581 entitled "REAL-TIME AUTOMATIC REGISTRATION FEEDBACK," filed on Jul. 2, 2015, by Brown et al.; U.S. patent application Ser. No. 14/753,229 entitled "METHODS FOR MARKING BIOPSY LOCATION," filed on Jun. 29, 2015, by Brown et al.; U.S. patent application Ser. No. 14/753,288 entitled "SYSTEM AND METHOD FOR NAVIGATING WITHIN THE LUNG," filed on Jun. 29, 2015, by Brown et al.; U.S. patent application Ser. No. 14/754,058 entitled "INTELLIGENT DISPLAY," filed on Jun. 29, 2015, by Kehat et al.; U.S. patent application Ser. No. 14/788,952 entitled "UNIFIED COORDINATE SYSTEM FOR MULTIPLE CT SCANS OF PATIENT LUNGS," filed on Jul. 1, 2015, by Greenburg et al.; U.S. patent application Ser. No. 14/709,395 entitled "ALIGNMENT CT," filed on Jul. 2, 2015, by Klein et al.; and U.S. patent application Ser. No. 14/751,257 entitled "DYNAMIC 3D LUNG MAP VIEW FOR TOOL NAVIGATION INSIDE THE LUNG," filed on Jul. 2, 2014, by Weingarten et al., the entire contents of all of which are hereby incorporated by reference.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in virtually any appropriately detailed structure. While the preceding embodiments were described in terms of bronchoscopy of a patient's airways, those skilled in the art will realize that the same or similar devices, systems, and methods may be used in other lumen networks, such as, for example, the vascular, lymphatic, and/or gastrointestinal networks as well.

What is claimed is:

1. A system for navigating to and interacting with a region of interest during a respiratory cycle, the system comprising:
   an extended working channel defining a lumen extending therethrough for receiving a tool;
   a sensor configured to sense movements of a patient;
   a computing device including a memory and at least one processor;
   a plurality of images stored in the memory;
   a display device that displays a user interface;
   the at least one processor configured to:
      determine movement of the tool during the respiratory cycle of the patient;
      obtain a location of the sensor at peak inhalation of the patient's respiratory cycle and at peak exhalation of the patient's respiratory cycle from the plurality of images stored in the memory;
      predict movement of the patient's airways and the region of interest during the respiratory cycle of the patient based on the determined movement of the tool and the obtained location of the sensor;
      determine, using the predicted movement of the patient's airways and the region of interest, a distance between a distal tip of the tool and the region of interest and an orientation of the distal tip of the tool with respect to the region of interest at peak inhalation of the patient's respiratory cycle and at peak exhalation of the patient's respiratory cycle;
      determine, for each of peak inhalation of the patient's respiratory cycle and peak exhalation of the patient's respiratory cycle, the distance that allows interaction between the distal tip and the region of interest and the orientation that allows interaction between the distal tip and the region of interest; and
      confirm that the determined distance and the determined orientation will allow interaction between the distal tip and the region of interest during the same peak of the patient's respiratory cycle; and
   a program stored in the memory that, when executed by the at least one processor, presents the user interface, the user interface including:
      an indication of which peak of the patient's respiratory cycle at which the determined distance and the determined orientation both likely allow interaction between the distal tip and the region of interest;
      at least one image of the plurality of images depicting the region of interest; and
      a probability diagnostic and/or treatment zone defining a probable distribution of a trajectory of the tool once deployed beyond an opening of the extended working channel displayed in the at least one image based on the predicted movement of the airways and the region of interest during the respiratory cycle.

2. The system according to claim 1, wherein each image of the plurality of images stored in the memory is composed of an inhalation image and an exhalation image.

3. The system according to claim 2, where the user interface is configured to depict movement of the region of interest, the extended working channel, and the airways during the respiratory cycle.

4. The system according to claim 3, where the user interface is configured to allow a user to position the probability diagnostic and/or treatment zone in a location and determine a position of the probability diagnostic and/or treatment zone at peak inhalation and at peak exhalation so that at least a portion of the region of interest is encompassed by the probability diagnostic and/or treatment zone.

5. The system according to claim 4, wherein the user interface is further configured to display the probability diagnostic and/or treatment zone with a first indicator and a second indicator,
   where the first indicator includes the determined distance between the distal tip of the tool and the region of interest, and
   the second indicator includes the determined orientation of the tool with respect to the region of interest.

6. The system according to claim 5, wherein when the portion of the region of interest is encompassed by the probability diagnostic and/or treatment zone, a status of the second indicator changes to indicate that the determined orientation of the tool allows the tool to interact with the region of interest.

7. The system according to claim 5, wherein when a range from the opening of the extended working channel to the region of interest is less than a maximum deployable range of the tool, a status of the first indicator changes to indicate that the determined distance of the tool allows the tool to interact with the region of interest.

8. The system according to claim 3, wherein the movement of the region of interest and the airways is asynchronous during inhalation and exhalation and depicted by changes of the probability diagnostic and/or treatment zone.

9. The system according to claim 1, wherein the user interface is further configured to allow a user to display the probability diagnostic and/or treatment zone as a three-dimensional volumetric shape.

10. The system according to claim 9, wherein the user interface is configured such that an increase in a region of interest volume inside the probability diagnostic and/or treatment zone indicates an increase in probability that the tool will interact with a portion of the region of interest inside the probability diagnostic and/or treatment zone.

11. The system according to claim 9, wherein the user interface is configured such that a length of the probability diagnostic and/or treatment zone from the opening of the extended working channel corresponds to a maximum effective range the tool can be deployed beyond the opening of the extended working channel.

12. The system according to claim 1, wherein the user interface is further configured to allow the user to display the probability diagnostic and/or treatment zone as a two-dimensional shape.

13. The system according to claim 1, wherein the plurality of images stored in the memory are images of the patient's airways during inhalation and exhalation obtained prior to a procedure performed on the patient and the at least one processor is configured to predict movement of the patient's airways and the region of interest during the respiratory cycle of the patient based on:
   the determined movement of the tool; and
   a comparison between the location of the sensor obtained from the plurality of images stored in the memory and a location of the sensor during at least one of peak inhalation or peak exhalation of the patient obtained during the procedure performed on the patient.

14. A system for navigating to and interacting with a region of interest, the system comprising:
   an electromagnetic (EM) field generator configured to generate an EM field;
   a plurality of sensors configured to sense movements of a patient based on the EM field;
   a memory storing a plurality of images;
   at least one processor communicable with the memory;
   a display device that displays a user interface;

wherein the at least one processor is configured to:
  determine movement of a tool during a respiratory cycle of a patient based on the EM field;
  obtain a location of the plurality of sensors at peak inhalation of the patient's respiratory cycle and at peak exhalation of the of the patient's respiratory cycle from the plurality of images stored in the memory;
  predict movement of the patient's airways and the region of interest during the respiratory cycle of the patient based on the determined movement of the tool and the obtained location of the plurality of sensors;
  determine, using the predicted movement of the patient's airways and the region of interest, a distance between a distal tip of the tool and the region of interest and an orientation of the distal tip of the tool with respect to the region of interest at peak inhalation of the patient's respiratory cycle and at peak exhalation of the patient's respiratory cycle;
  determine, for each of peak inhalation of the patient's respiratory cycle and peak exhalation of the patient's respiratory cycle, the distance that allows interaction between the distal tip and the region of interest and the orientation that allows interaction between the distal tip and the region of interest; and
  confirm that the determined distance and the determined orientation will allow interaction between the distal tip and the region of interest during the same peak of the patient's respiratory cycle; and
wherein a program stored in the memory that, when executed by the at least one processor, presents the user interface including:
  an indication of which peak of the patient's respiratory cycle at which the determined distance and the determined orientation both allow interaction between the distal tip and the region of interest;
  at least one image of the plurality of images depicting the region of interest; and
  a probability diagnostic and/or treatment zone defining a probable distribution of a trajectory of the tool once deployed beyond an opening of a catheter displayed in the at least one image based on the predicted movement of the airways and the region of interest during the respiratory cycle.

15. The system according to claim 14, wherein the plurality of sensors are reference sensors located on a chest of the patient and configured to sense movement of the chest at a corresponding location based on the EM field.

16. The system according to claim 15, wherein the at least one processor is further configured to determine movements of the chest based on sensed results from the plurality of reference sensors.

17. The system according to claim 14, wherein the tool includes an EM sensor configured to sense a location of the tool based on the EM field.

18. The system according to claim 14, wherein the plurality of images stored in the memory are images of the patient's airways during inhalation and exhalation obtained prior to a procedure performed on the patient and the at least one processor is configured to predict movement of the patient's airways and the region of interest during the respiratory cycle of the patient based on:
  the determined movement of the tool; and
  a comparison between the location of the plurality of sensors obtained from the plurality of images stored in the memory and a location of the plurality of sensors during at least one of peak inhalation or peak exhalation of the patient obtained during the procedure performed on the patient.

19. An apparatus for compensating respiratory movements, the apparatus comprising:
  a memory storing a plurality of images;
  a network interface configured to receive movement information of a tool navigating through a luminal network of a patient;
  a sensor configured to sense movements of the patient;
  at least one processor configured to:
    determine movement of the tool in the luminal network of the patient during a respiratory cycle of the patient;
    obtain a location of the sensor at peak inhalation of the patient's respiratory cycle and at peak exhalation of the patient's respiratory cycle from the plurality of images stored in the memory;
    predict movement of the patient's airways and a region of interest during the respiratory cycle of the patient based on the determined movement of the tool and the obtained location of the sensor;
    determine, using the predicted movement of the patient's airways, a distance between a distal tip of the tool and the region of interest and an orientation of the distal tip of the tool with respect to the region of interest at peak inhalation of the patient's respiratory cycle and at peak exhalation of the patient's respiratory cycle;
    determine, for each of peak inhalation of the patient's respiratory cycle and peak exhalation of the patient's respiratory cycle, the distance that allows interaction between the distal tip and the region of interest and the orientation that allows interaction between the distal tip and the region of interest; and
    confirm that the determined distance and the determined orientation will allow interaction between the distal tip and the region of interest during the same peak of the patient's respiratory cycle; and
  a program stored in the memory that, when executed by the at least one processor, presents a user interface including:
    an indication of which peak of the patient's respiratory cycle at which the determined distance and the determined orientation both allow interaction between the distal tip and the region of interest;
    at least one image of the plurality of pre-operative images depicting the region of interest; and
    a probability diagnostic and/or treatment zone defining a probable distribution of a trajectory of the tool once deployed beyond an opening of a catheter displayed in the at least one image based on the predicted movement of the airways and the region of interest during the respiratory cycle.

* * * * *